(12) United States Patent
Jassal et al.

(10) Patent No.: US 11,480,523 B2
(45) Date of Patent: Oct. 25, 2022

(54) CHEMICAL TESTING DEVICE WITH A SAMPLE CHAMBER HAVING A PISTON THEREIN WITH A CHAMBER SEALING ELEMENT THEREON

(71) Applicant: ADEY HOLDINGS (2008) LIMITED, Cheltenham (GB)

(72) Inventors: Mukash Jassal, Cheltenham (GB); Simon Downie, Cheltenham (GB)

(73) Assignee: ADEY HOLDINGS (2008) LIMITED, Cheltenham (GB)

( * ) Notice: Subject to any disclaimer, the term of this patent is extended or adjusted under 35 U.S.C. 154(b) by 391 days.

(21) Appl. No.: 16/634,613

(22) PCT Filed: Jul. 27, 2018

(86) PCT No.: PCT/EP2018/070497
§ 371 (c)(1),
(2) Date: Jan. 28, 2020

(87) PCT Pub. No.: WO2019/020816
PCT Pub. Date: Jan. 31, 2019

(65) Prior Publication Data
US 2020/0271579 A1    Aug. 27, 2020

(30) Foreign Application Priority Data

Jul. 28, 2017  (GB) ...................... 1712175

(51) Int. Cl.
*G01N 21/64* (2006.01)
*G01N 21/15* (2006.01)
(Continued)

(52) U.S. Cl.
CPC ......... *G01N 21/64* (2013.01); *F24D 19/0092* (2013.01); *G01N 21/15* (2013.01); *G01N 33/18* (2013.01); *G01N 2201/1288* (2013.01)

(58) Field of Classification Search
CPC ........ G01N 21/15; G01N 21/64; G01N 33/18; G01N 33/182; F24D 19/0092
(Continued)

(56) References Cited

U.S. PATENT DOCUMENTS 3,225,645 A * 12/1965 Baruch ................. G01N 35/00
                                                    250/576
3,401,591 A *  9/1968 Anthon ................. G01N 35/00
                                                    356/36

(Continued)

FOREIGN PATENT DOCUMENTS

DE        20102894 U1     3/2002
DE     102004048333 A1    4/2006
(Continued)

*Primary Examiner* — Arlen Soderquist
(74) *Attorney, Agent, or Firm* — Jacob M. Ward; Ward Law Office LLC

(57) ABSTRACT

A testing device (10) for testing the level of a selected chemical in central heating system water in a central heating system circuit comprises: a sample chamber (14) for holding a sample of central heating system water to be tested, the sample chamber (14) being connectable (12) to the central heating system circuit to allow fluid to pass between the central heating system circuit and the sample chamber (14); means (16) for controlling filling of the sample chamber (14) with central heating system water from the central heating system circuit, and emptying of the sample chamber (14); at least one valve (18) for isolating the sample of central heating system water from the heating circuit during testing; and optical testing apparatus including a light source (20) and a detector (22), for measuring an optical property of the sample of central heating system water isolated within the sample chamber (14) and thereby making a determination as to whether or not the level of the selected chemical in the water is greater than a predetermined threshold level.

23 Claims, 8 Drawing Sheets

(51) Int. Cl.
    *G01N 33/18*     (2006.01)
    *F24D 19/00*     (2006.01)

(58) Field of Classification Search
    USPC .............................. 422/82.05; 436/54, 165
    See application file for complete search history.

(56) References Cited

U.S. PATENT DOCUMENTS

| | | | | |
|---|---|---|---|---|
| 3,489,521 A | * | 1/1970 | Buckle | G01N 35/02 |
| | | | | 422/65 |
| 3,652,170 A | * | 3/1972 | Beer | G01N 35/1095 |
| | | | | 250/576 |
| 3,781,116 A | * | 12/1973 | Jones | G01N 21/03 |
| | | | | 356/246 |
| 4,169,125 A | * | 9/1979 | Rodriguez | G01N 35/026 |
| | | | | 422/65 |
| 4,194,391 A | * | 3/1980 | Rosenberger | G01N 15/04 |
| | | | | 356/442 |
| 4,715,710 A | * | 12/1987 | Andersen | G01N 21/276 |
| | | | | 356/244 |
| 4,980,130 A | * | 12/1990 | Metzger | G01N 1/38 |
| | | | | 422/65 |
| 5,061,634 A | * | 10/1991 | Hickey | G01N 21/82 |
| | | | | 436/52 |
| 6,255,118 B1 | | 7/2001 | Alfano et al. | |
| 6,386,017 B1 | * | 5/2002 | Hewitt | G01N 15/06 |
| | | | | 73/61.42 |
| 8,850,903 B2 | | 10/2014 | Curtis et al. | |
| 2005/0145550 A1 | | 7/2005 | Loyd et al. | |
| 2005/0276724 A1 | * | 12/2005 | Bremauer | B01F 35/754251 |
| | | | | 422/68.1 |
| 2006/0160226 A1 | | 7/2006 | Johnson | |
| 2007/0178595 A1 | * | 8/2007 | Raghuraman | G01N 21/80 |
| | | | | 436/43 |
| 2008/0019873 A1 | * | 1/2008 | Shah | G01N 1/405 |
| | | | | 422/68.1 |
| 2009/0107921 A1 | | 4/2009 | Chen et al. | |
| 2010/0050760 A1 | * | 3/2010 | Vannuffelen | E21B 49/10 |
| | | | | 166/264 |
| 2013/0335731 A1 | | 12/2013 | Jorden | |
| 2014/0264077 A1 | | 9/2014 | Tokhtuev et al. | |
| 2015/0198037 A1 | * | 7/2015 | Van Hal | G01N 33/20 |
| | | | | 702/22 |
| 2015/0241344 A1 | | 8/2015 | Mattejat | |
| 2016/0273786 A1 | | 9/2016 | Day | |
| 2020/0225125 A1 | * | 7/2020 | Jassal | C02F 5/08 |

FOREIGN PATENT DOCUMENTS

| | | |
|---|---|---|
| DE | 102007055132 A1 | 5/2009 |
| EP | 2270471 A1 | 1/2011 |
| GB | 2434861 A | 8/2007 |
| GB | 2462518 A | 2/2010 |
| GB | 2473081 A | 3/2011 |
| GB | 2490898 A | 11/2012 |
| GB | 2494073 A | 2/2013 |
| GB | 2508257 A | 5/2014 |
| GB | 2513693 A | 11/2014 |
| GB | 2550351 A | 11/2017 |
| GB | 2555798 A | 5/2018 |
| JP | H11319885 A | 11/1999 |
| JP | 2003164852 A | 6/2003 |
| WO | 8908227 A | 9/1989 |
| WO | 8909227 A | 9/1989 |
| WO | 2007143047 A1 | 12/2007 |

\* cited by examiner

CHEMICAL TESTING DEVICE WITH A SAMPLE CHAMBER HAVING A PISTON THEREIN WITH A CHAMBER SEALING ELEMENT THEREON

CROSS-REFERENCE TO RELATED APPLICATIONS

This patent application is a United States National Stage of International Patent Application No. PCT/EP2018/070497, filed on Jul. 27, 2018, which in turn claims priority to Great Britain Patent Application No. 1712175.7, filed on Jul. 28, 2017. The entire disclosures of the above patent applications are hereby incorporated herein by reference.

TECHNICAL FIELD

The present invention relates to measuring the level of a chemical in a sample, particularly to measuring the level of a corrosion inhibitor chemical in central heating system water.

BACKGROUND TO THE INVENTION

It is well known that wet central heating systems suffer from internal corrosion. Steel on the inside surfaces of radiators, in the presence of water circulating through the system and oxygen which is inevitably dissolved in the water to some extent, is prone to rust. Due to corrosion, particles will become detached from the damaged internal surfaces of radiators and become entrained in the system water. These particles can then cause damage to boilers, especially modern high-efficiency boilers which have very narrow channels in the heat exchanger. The presence of the particles also reduces the efficiency of heat transfer, leading to higher fuel use.

Managing this problem is therefore important to prevent premature boiler failure and ensure efficient operation. The amount of particulate contamination in system water can be reduced by the use of a magnetic filter, which continually captures particles and removes them from the system flow. Filters are available which are effective to remove both magnetic and non-magnetic particles—see for example GB2508257.

However, using a magnetic filter on its own will not prevent corrosion and will not therefore solve the problem of magnetic particles being generated in the first place. In a system which is particularly prone to corrosion, the volume of particles being added to the system water may exceed the rate at which they can be removed by a magnetic filter with a reasonable service interval. Best practice for ensuring an efficient and reliable system therefore includes dosing the system water with an inhibitor chemical, to reduce corrosion and therefore reduce the rate at which particulate contamination builds up in system water. In principle, a sealed system correctly dosed with an inhibitor can remain stable for many years. However, factors which vary between systems mean that over time, the inhibitor chemical can become diluted and/or degrade. One way of managing this is simply to use a "rule of thumb" to top up the inhibitor in a system by adding a bottle say, every twelve months. Modest overdosing of inhibitor is unlikely to cause any technical problems, but adding inhibitor unnecessarily is expensive.

It is an object of the present invention to solve this problem by providing a means for testing whether or not central heating system water is correctly dosed with an inhibitor chemical.

STATEMENT OF INVENTION

According to the present invention, there is provided a testing device for testing the level of a selected chemical in central heating system water in a central heating system circuit, the device comprising:
  a sample chamber for holding a sample of central heating system water to be tested, the sample chamber being connected to the central heating system circuit to allow fluid to pass between the central heating system circuit and the sample chamber;
  means for controlling filling of the sample chamber with central heating system water from the central heating system circuit, and emptying of the sample chamber;
  at least one valve for isolating the sample of central heating system water from the heating circuit during testing; and
  optical testing apparatus including a light source and a detector, for measuring an optical property of the sample of central heating system water isolated within the sample chamber and thereby making a determination as to whether or not the level of the selected chemical in the water is greater than a predetermined threshold level.

The device of the invention allows for automated in-situ sample testing of central heating system water, to determine whether or not it is dosed with the correct level of a selected chemical. The selected chemical is generally a corrosion inhibitor, although it is possible that the concentration of other types of chemicals in central heating system water could be monitored by embodiments of the invention, if required. By using the device of the invention, the system can be kept dosed with the correct level of inhibitor to limit corrosion, without wasting inhibitor.

Preferably, the sample chamber is emptied by returning the central heating system water to the central heating system circuit. This ensures that there is no loss of pressure in the central heating system circuit. If the quantity is small enough, it may be acceptable in some embodiments to empty the water into a drain after testing, but over time this will inevitably cause a loss of system pressure, and topping up the system will result in dilution of the inhibitor chemical.

Preferably, there is a single flow passage between the sample chamber and the central heating system circuit, to allow fluid to pass in both directions between the central heating system circuit and the sample chamber.

The sample chamber is preferably light transmissible, at least in the range of operation of the optical testing apparatus. This allows the optical testing apparatus to be mounted outside of the sample chamber. In one embodiment, the sample chamber is made from borosilicate glass. Preferably, the optical testing apparatus and sample chamber are enclosed by a light-proof enclosure, or at least an enclosure which substantially blocks any wavelengths which would interfere with the optical testing apparatus.

The means for controlling filling and emptying of the sample chamber may be in the form of a piston. Preferably, the piston includes a wiper seal which seals against the internal sides of the sample chamber. The piston can be retracted to draw water out of the central heating system circuit into the sample chamber, remain retracted while testing takes place, and then be extended to empty the sample chamber and return the water to the central heating system circuit. Emptying the sample chamber after each testing operation prevents dulling of the light-transmissible sample chamber by a build-up of dirt from the water onto surfaces of the sample chamber.

Where a piston is used, the valve for isolating the sample during testing may be integrated into the piston, so that when the piston is in a fully retracted position, having drawn water into the sample chamber, a sealing element on the piston seals the entrance to the sample chamber, preventing any further flow between the sample chamber and the central heating system circuit.

A piston with an integrated valve may include a necked-down section in front of the piston crown, to attach the valve to the piston whilst allowing water to flow into the sample chamber, around the necked-down section. Alternatively, the piston might include a slot along one side (in principle, this may be considered an asymmetric necking-down of the piston, in front of the crown). The necked-down section of the piston, in either alternative, will be present in the sample chamber during testing. The shape and optical characteristics of the necked-down piston therefore need to be selected so that either the necked-down section of the piston does not interact with the optical testing apparatus, or that any interaction is predictable so that it can be systematically accounted for, or insignificant enough to be ignored. A slotted piston/asymmetrically necked-down piston, may allow the necked-down portion of the piston to be located "out of sight" of the optical testing apparatus.

As an alternative, a valve may be provided independently of the piston. For example, a motorised ball valve may be provided between the central heating system circuit and the sample chamber.

The testing process is preferably fully automatic, with control means being adapted to draw water into the sample chamber (for example by operating a motorised piston), seal the sample chamber by closing the valve (if the valve needs to be operated independently of the piston), test the sample with the optical testing apparatus, including making a determination as to whether or not the level of the selected chemical is acceptable, and then open the valve and empty the chamber. Preferably, there may be a time delay of, for example, ten minutes, between closing the valve and testing the sample. This is to allow for any particulate contamination in the sample to settle, whilst the sample is held in the static test chamber, so that any particles suspended in the system water do not affect the reading from the optical testing apparatus.

In some embodiments, a filter mesh could be provided between the sample chamber and the central heating system, in order to prevent particles from entering the sample chamber. However, there are problems with this approach including an increase of power consumption when operating the piston, due to the resistance caused by the filter mesh.

As an alternative, a magnet may be provided for attracting any magnetic particles which may be entrained in the water being tested. Preferably, the magnet may be movable between an in-use position where the magnet produces a magnetic field in the sample chamber, and an out-of-use position where the magnet is located away from the sample chamber and produces no significant magnetic field in the sample chamber. During testing, the magnet may be brought into the in-use position once the sample chamber is sealed. Any magnetic particles in the sample chamber will then be drawn towards the magnet and removed from the main body of water in the sample chamber, clearing the water. Once testing is complete, the magnet may be moved to the out-of-use position and magnetic particles will be returned to the water.

Temporarily holding magnetic particles using a movable magnet ensures that the water is clear of magnetic particles during testing. This, in combination with allowing a few minutes for the water to settle before testing, ensures that turbidity does not influence the testing process. At the same time, since the magnet is removed after testing, magnetic particles do not build up in the sample chamber. The device is not designed to permanently remove magnetic particles from central heating system water, and it is envisaged that it would be used in combination with a magnetic filter on the heating system circuit, which is cleaned regularly. However, providing the movable magnet ensures that low levels of magnetic particles remaining in the system water do not interfere with the testing process.

Preferably, the magnet is provided on the outside of the sample chamber, the magnet in the in-use position being disposed against the outside of the wall of the sample chamber, and the magnet in the out-of-use position being disposed in a position outside the sample chamber, and spaced from the wall of the sample chamber. The magnet may be mounted on a pivoting arm to facilitate movement between the in-use position and the out-of-use position. The pivoting arm may be arranged to automatically pivot as the piston is operated to draw fluid into and out of the chamber, so that the magnet is in the in-use position when the chamber is full and in the out-of-use position when the chamber is empty.

The selected chemical is in most cases a corrosion inhibitor, although measurement of the level of other chemicals is possible using apparatus according to the invention. In many embodiments, the optical testing apparatus may measure the level of the selected chemical indirectly, in that a tracer chemical is first added to the corrosion inhibitor (or other selected chemical), and it is the tracer chemical which is directly measured by the optical testing means. A tracer chemical can be chosen which has similar stability to the selected chemical (i.e. any degradation of the tracer chemical is approximately the same as degradation of the selected chemical), so that the quantity of tracer chemical detected in the system water is a reliable indication of the quantity of the selected chemical which is present. A fluorescent dye tracer which has been found to give good results with typical corrosion inhibitors is 1,3,6,8 Pyrenetetrasulfonic acid tetrasodium salt (PTSA). This fluorescent dye is found to be reasonably stable within typical inhibitor chemicals, in the temperature conditions typical of a heating system. When excited with a 375 nm source, PTSA exhibits fluorescence at 405 nm. In a typical inhibitor, a concentration of 200-400 mg of tracer per litre of inhibitor is found adequate. This would give a concentration of about 0.8-1.6 mg of tracer per litre of system water, when correctly fully dosed. An 'acceptable' level of inhibitor might typically be around 0.8 mg of tracer per litre of system water. When a lower levels of tracer is detected then the device should indicate that a top-up of inhibitor is required.

An embodiment of an optical testing apparatus suitable for measuring fluorescence includes a light source for exciting the (tracer) chemical—where PTSA is used as described above the excitation light source would need to emit at least at 375 nm, and a detector for detecting emitted light at the emission wavelength—in this example 405 nm. The intensity of the detected emitted light at 405 nm is directly proportional to the concentration of the fluorescent tracer chemical in the sample, and so a determination can be made simply based on whether the intensity of the detected light exceeds a threshold or not.

Preferably, the excitation light source is an LED, and the detector is a photodiode. In one embodiment, the excitation light source and detector are placed at an acute angle to each other, facing into a substantially cylindrical borosilicate glass sample chamber. As an alternative, the light source and detector could be disposed at an obtuse angle, perpendicularly to each other or directly opposite each other.

Depending on the excitation light source and the detector used in specific embodiments, it may be necessary or desirable to include filter(s) before the detector to allow only light emitted from the fluorescent tracer through and to limit any interference from the excitation source. Preferably, a narrow band LED is used, but to reduce costs a wider band excitation light source together with filter(s) on the emitter and/or on the detector is a possibility.

The optical property of PTSA which is measured by the device is fluorescence. However, it is also possible to envisage alternative embodiments of the invention, using different tracers or inherent optical properties of the selected chemical, where the optical property measured is, for example, absorption or phosphorescence.

It is envisaged that the device would automatically operate to perform a test, for example once a fortnight or once a month. This is frequent enough to ensure that a central heating system is not left for any significant period of time with inadequate inhibitor, but also at this testing interval the device can be battery powered by, for example, a PP3 battery which will last a reasonable length of time.

A calibration element may be provided within the sample chamber. Preferably, the calibration element is moved into the sample chamber automatically when the sample chamber is emptied, and moved out of the sample chamber again when water is drawn into the sample chamber for testing. In a preferred embodiment, the calibration element is provided as part of the piston, so that the calibration element moves into the sample chamber when the piston extends. The calibration element in one embodiment is a plastic part treated with a coating which causes it to fluoresce with similar characteristics to the tracer chemical used, with a known and constant intensity. Typically, calibration takes place as part of the automated testing cycle, before each and every sample test takes place.

The device may output the result of the test as simply as (for example) a red LED which lights to indicate inadequate inhibitor concentration, and a green LED which lights to indicate adequate inhibitor concentration. It is envisaged that more advanced embodiments will be able to transmit test results, for example wirelessly by NFC or Bluetooth® or WiFi or another radio frequency communication technology, or over wired communication channels. Some embodiments may be integrated into a central heating system boiler in which case they may transmit test results to the boiler data management system.

Some embodiments may include data storage means, for storing historical test results which can be read out on output means or downloaded onto another device.

In some embodiments, the device could include an inhibitor reservoir and means of introducing inhibitor into the central heating system water. When the test indicates that the inhibitor concentration is too low, the system can then be automatically dosed to recover the correct concentration of inhibitor.

As an alternative, a separate dosing device including an inhibitor reservoir and means of introducing inhibitor into the central heating system water may be provided on the same heating system, the testing device being arranged to communicate with the dosing device to cause dosing of the system water in response to a test result indicating that dosing is required. Ideally a (wired or wireless) electronic signal can be sent by the testing device to the dosing device to cause dosing of the system when an insufficient inhibitor concentration is detected.

In addition to the optical testing apparatus for determining whether the concentration of the selected chemical is acceptable, the device may include testing apparatus for testing the turbidity, pH, and/or conductivity of central heating system water in the sample chamber. Turbidity can be measured with optical testing apparatus, particularly an emitter and a detector, which may work with a relatively broad spectrum of light. A test for turbidity ideally takes place very shortly after water has been drawn into the sample chamber, before any suspended particles have time to settle. Turbidity provides a measure of the level of particulate contamination, and an excess might indicate that a magnetic filter in the system has reached capacity and needs to be cleaned. Where a movable magnet is provided, the test for turbidity may take place with the magnet in the out-of-use position. In some embodiments, one turbidity measurement could take place with the magnet in the in-use position, and one turbidity measurement could take place with the magnet in the out-of-use position, the difference between those two measurements being used as an indication of the level of turbidity due to magnetic particles. pH and conductivity can be measured by known types of probes, which need to be in contact with water in the sample chamber. It is important to ensure that the pH of system water is low enough that its alkalinity will not attack aluminium surfaces within the system, for example aluminium radiators or boiler heat exchangers. Electrical conductivity can be a useful measure of the level of dissolved salts in the system water, that could result in scale formation.

According to a second aspect of the invention, there is provided a method of testing central heating system water for the concentration of a selected chemical, the method comprising:

drawing a sample of central heating system water into a sample chamber;

waiting for a period of time to allow suspended solids to settle out of the water in the sample chamber;

activating optical testing apparatus including a light source and a detector, to measure an optical property of the sample and thereby make a determination as to whether or not the level of the selected chemical in the water is greater than a predetermined threshold;

emptying the sample chamber.

According to a third aspect of the invention, there is provided an automatic dosing device for dosing central heating system water with a chemical, the dosing device including a fitment for permanently attaching the dosing device into a central heating system circuit, a chemical reservoir, a passageway in the fitment between the central heating system circuit and the chemical reservoir, a valve in the passageway, and means for introducing chemical from the chemical reservoir into the central heating system circuit in response to an electronic signal.

The electronic signal may be a signal from a testing device according to the first aspect of the invention. When the signal indicates that dosing is required, chemical will be introduced into the central heating system circuit from the reservoir, through the passageway. When dosing is not required, the valve in the passageway will be closed so that the reservoir is not fluidly connected to the central heating system circuit.

Working together, a testing device may test for inhibitor concentration, and in response to a signal from the testing device, a dosing device may add inhibitor to the system to correct an insufficient concentration.

In one embodiment, the chemical reservoir is in the form of a syringe, the syringe having a piston driven by an electronic actuator. In this embodiment, the valve may be a check valve which allows fluid to flow from the reservoir to the central heating system circuit, but not in the other direction. When the piston is extended into the syringe, fluid will be forced from the reservoir, through the check valve and into the central heating system via the passageway in the fitment. Increased pressure in the syringe as a result of the syringe piston being operated will cause the check valve to open and allow fluid to flow into the central heating system circuit.

The actuator may be an electric motor. The motor may rotationally drive a screw, which in turn causes an arm to move linearly, pressing the back of the piston into the syringe, to dose the system with chemical.

In an alternative embodiment, the reservoir is pressurised to a greater static pressure than the central heating system, and the valve is a motorised valve or another electronically actuated valve. For example, a solenoid valve may be suitable in some embodiments. In this embodiment, the valve may be opened for a period of time in response to the electronic signal, and this will result in fluid flowing out of the high pressure reservoir and into the lower pressure central heating system.

The reservoir may be provided in the form of a pressurised canister, which includes a press-to-open valve on the nozzle. When fitted to the fitment of the dosing device, the canister may be held against a seat so that the valve on the nozzle of the canister is permanently open while the canister is fitted. The seat is at the entrance to the passageway on the fitment. Holding the canister in place may be achieved by a clamping arrangement which pushes the canister against the seat and retains it in position. With the valve on the canister nozzle permanently open, it will be the electronically actuated valve which controls flow of fluid from the canister into the central heating system circuit. However, when the canister needs to be removed and replaced the valve on the canister nozzle will close as the canister is removed.

Preferably a switch or sensor is provided to detect when the canister has been removed, and inhibit operation of the electronically actuated valve to ensure that the electronically actuated valve remains closed when the canister is not fitted. As an alternative or in addition, a one way check valve could be provided to prevent any flow of fluid out of the central heating system circuit when the canister is removed or depressurized.

In another alternative embodiment, the reservoir may again be provided in the form of a pressurized canister having a press-to-open valve on the nozzle. However, the pressurized canister may be located with the nozzle against a seat so that the nozzle is closed in a resting position. When an electronic signal is received and dosing is required, an electronic actuator may be arranged to press the canister against the seat to open the nozzle and allow fluid to flow from the canister into the central heating system circuit. According to a fourth aspect of the invention, there is provided a combined testing and dosing device, according to the first and third aspects of the invention.

In combination, a testing and dosing device work together to protect a central heating system, by continually monitoring the concentration of corrosion inhibitor present in the system water.

DESCRIPTION OF THE DRAWINGS

For a better understanding of the present invention and to show more clearly how it may be carried into effect, preferred embodiments will now be described with reference to the accompanying drawings, in which.

DESCRIPTION OF PREFERRED EMBODIMENTS

Figure 1:
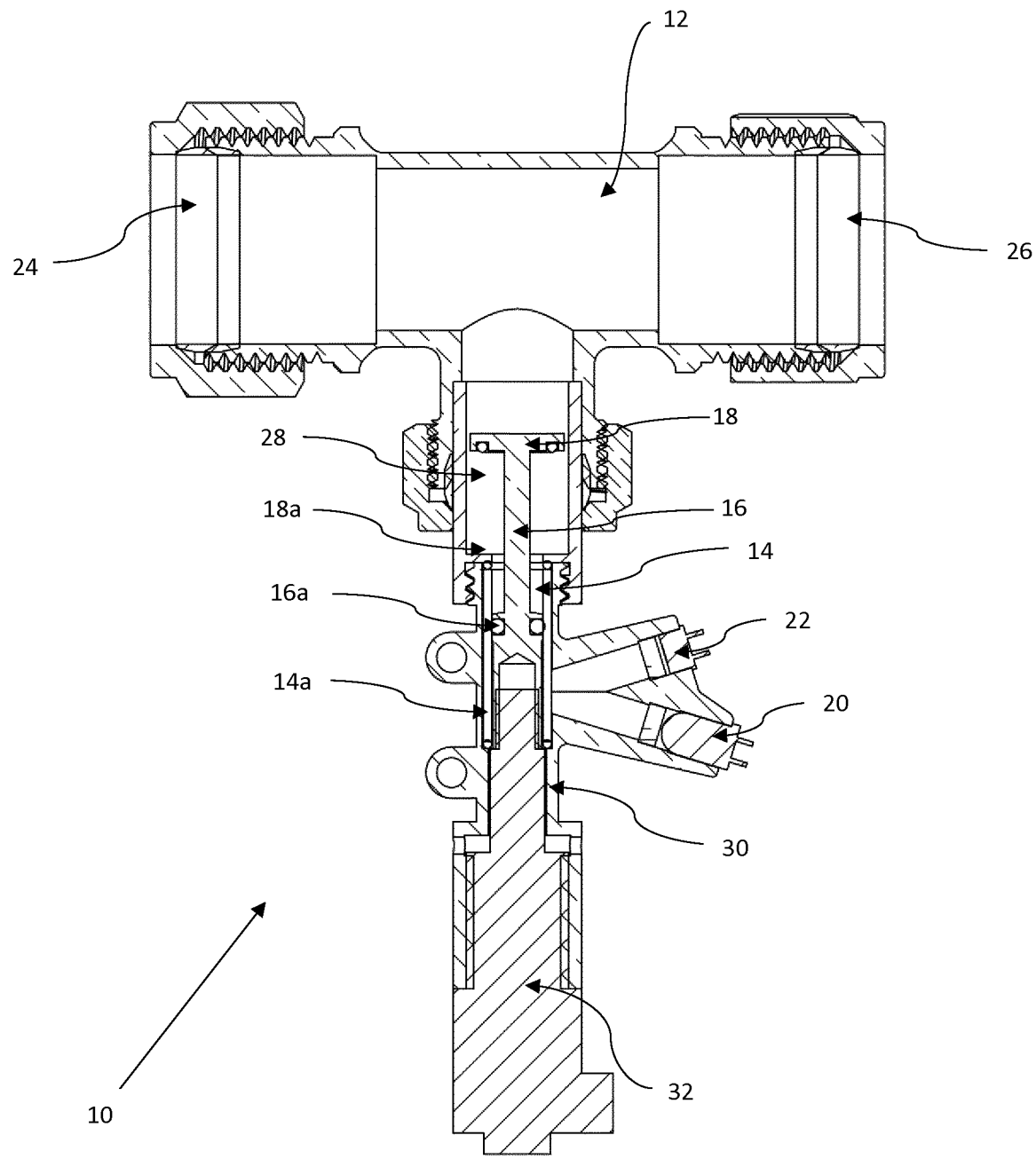
FIG. 1 shows a cross section through a first embodiment of a testing device according to the first aspect of the invention.

Referring firstly to FIG. 1, a first embodiment of a testing device according to the invention is generally indicated at 10. The testing device 10 comprises a fitment or connector 12 for connecting the testing device 10 into a central heating system circuit, a sample chamber 14 for holding an isolated sample of central heating system water during testing, means for controlling filling of the sample chamber 14 in the form of a motorised piston 16 having an integrated valve 18 for sealing the sample chamber 14 when the piston is retracted, and optical testing apparatus including an excitation light source 20 and a detector 22.

The connector 12 is in the form of a simple T-shaped connector, allowing central heating system water to flow (for example) into an inlet port 24 and out of an outlet port 26. In this embodiment, the connector 12 is symmetrical and so the inlet 24 and outlet 26 could be swapped, i.e. with central heating system water flowing in the other direction. The connector 12 connects the sample chamber 14 into the central heating system circuit, so that samples of central heating system water can be drawn into the sample chamber and tested automatically, whenever required.

In this embodiment, the connector 12 is in the form of a reducing T, i.e. the inlet and outlet ports are 22 mm compression fittings, and the branch of the T which connects to the sample chamber 14 is smaller in diameter. As an alternative to compression fittings, push-fit fittings or any other suitable fittings may be provided, for connecting the device into a central heating system circuit. Also, different sizes of device may be provided for central heating systems using pipe diameters larger or smaller than 22 mm.

As an alternative to a T-shaped connector, a Y-shaped connector, or any other suitable shape may be used.

The walls 14a of the sample chamber 14 are made from borosilicate glass, which is transparent and highly resistant to thermal shock. The sample chamber 14 is a substantially cylindrical tube. A flow passage 28 is provided between the sample chamber 14 and connector 12, for allowing water to pass from the central heating system circuit into the sample chamber 14, and back again from the sample chamber 14 into the central heating system circuit.

To control filling and emptying of the sample chamber 14, the piston 16 can be extended into the sample chamber to empty the sample chamber 14, or retracted to fill it. In FIG. 1 the piston 16 is shown in an intermediate position; a fully-extended position would be further towards the top of FIG. 1, and a fully-retracted position would be further towards the bottom. The piston 16 includes an O-ring wiper seal 16a, which prevents any water getting behind the seal 16a (i.e. below the seal 16a in FIG. 1). The wiper seal 16a also acts to clean the borosilicate glass walls 14a of the sample chamber 14 after each use, to prevent dulling of the walls 14a and a reduction in light-transmissibility due to accumulation of dirt.

In this embodiment, the piston includes an integrated valve 18. When the piston is fully retracted (i.e. all the way downwards in FIG. 1), the valve 18 engages with a valve seat 18a to seal the sample chamber from the central heating system circuit, and keep the water sample static and isolated.

The excitation light source 20 and detector 22 are provided at an acute angle to each other, facing towards the sample chamber 14 on the outside of the borosilicate glass wall. An opaque moulding 30 is provided which houses the borosilicate glass tube sample chamber 14, and provides a mounting for the light source 20 and detector 22. The opaque moulding 30 prevents any light entering the sample chamber 14 from outside, controls the incidence of light on the sample chamber from the light source 20, and ensures that the light source 20 and detector 22 remain in a fixed position relative to each other, for consistency of measurements.

A stepper motor 32 is provided to move the piston 16 between the retracted and extended positions on a screw thread. Another type of actuator, for example a solenoid or another linear actuator, may be suitable in other embodiments.

Figure 2:
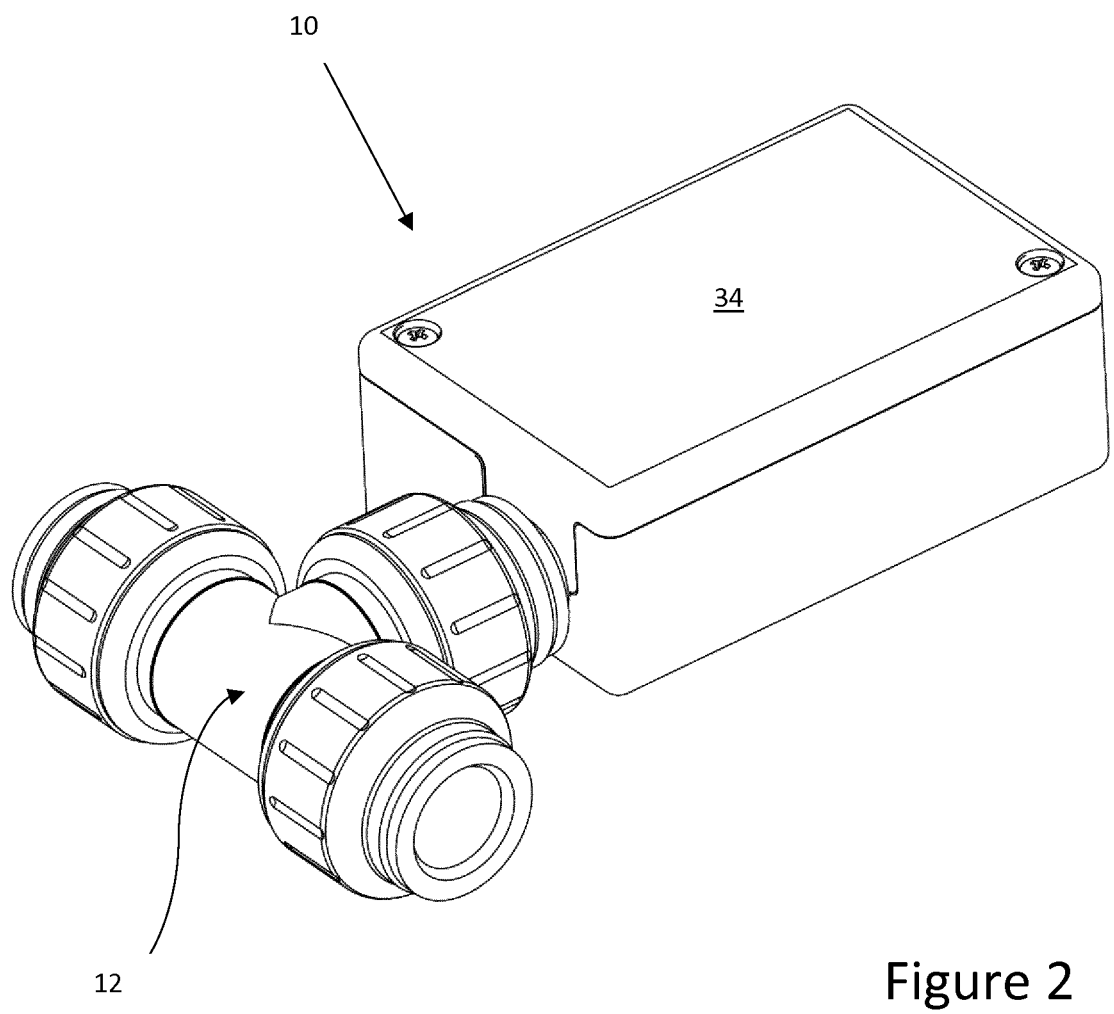
FIG. 2 shows a perspective view of the testing device of FIG. 1, with an outer casing fitted.

Referring now to FIG. 2, the same embodiment is shown, fitted with an outer casing 34. The outer casing encloses substantially all of the components of the testing device 10, with only the connector 12 extending out of the casing, for connection to a central heating system circuit. In addition to the components described and shown in FIG. 1, the casing 34 houses a control PCB and a battery to power the device. In some embodiments, an AC/DC transformer may be provided either internally of the casing 34 or externally, instead of a battery.

Figure 3:
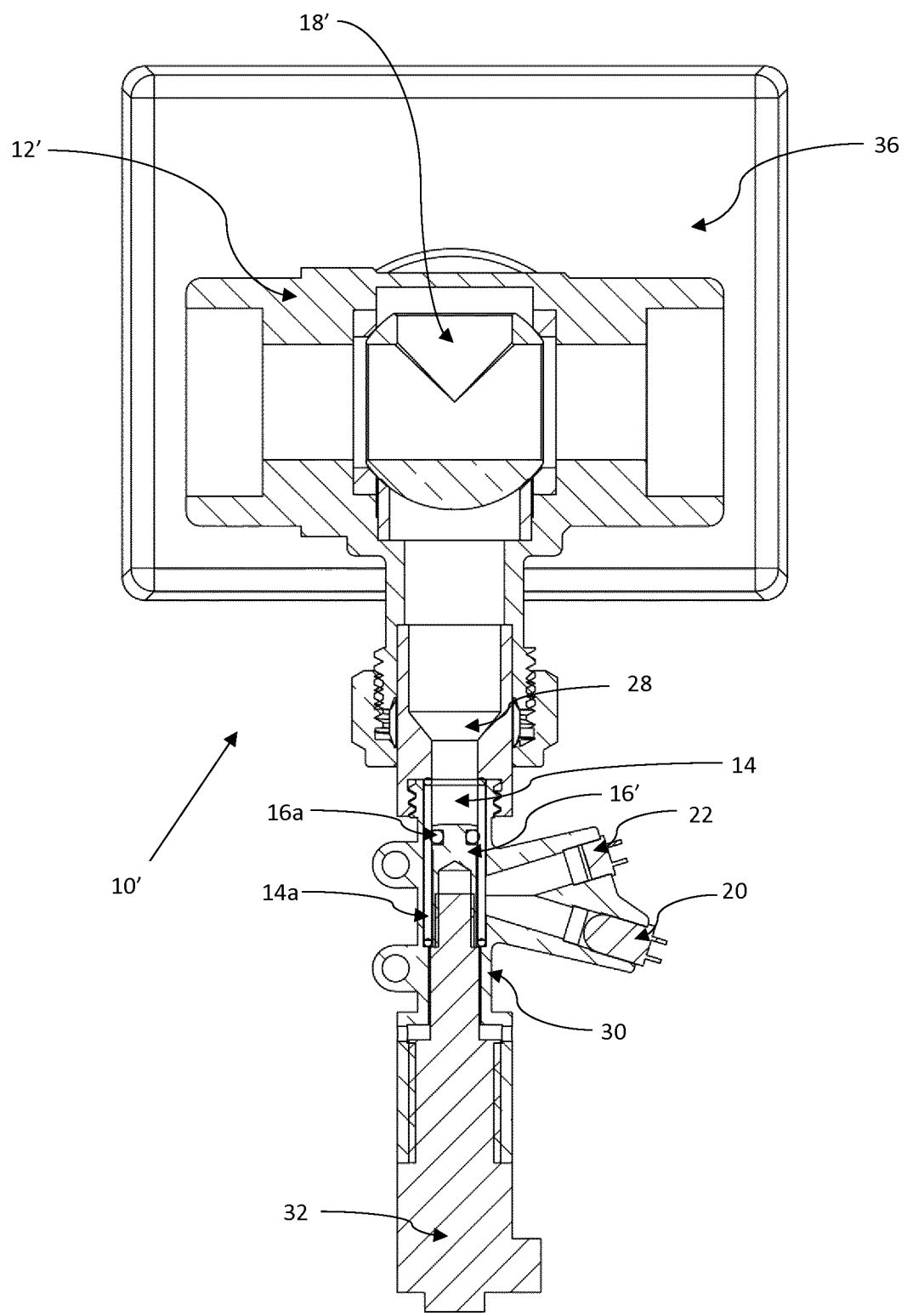
FIG. 3 shows a cross section through a second embodiment of a testing device according to the first aspect of the invention.
Figure 4:
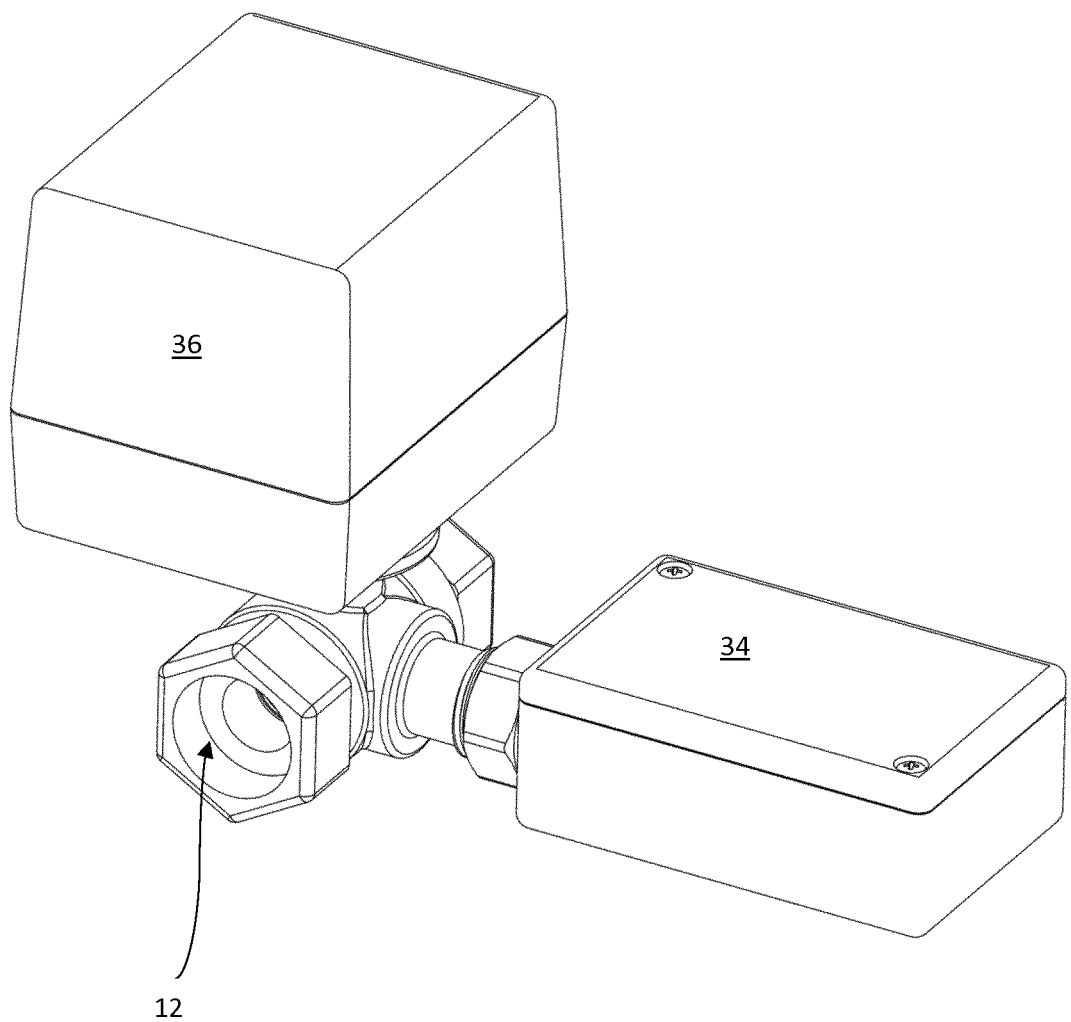
FIG. 4 shows a perspective view of the testing device of FIG. 3, with an outer casing fitted.

FIG. 3 illustrates an alternative embodiment of a testing device 10'. In most respects this embodiment is similar to the embodiment of FIG. 1, and like parts are labelled with like reference numerals. However, instead of the valve (18) integrated with the piston (16), the alternative embodiment uses a motorised ball valve 18', disposed in the connector 12, to seal the sample chamber 14 from the central heating circuit. The ball valve 18' is operated by an separate motor (not visible in the figures), and not by the stepper motor 32 which operates the piston 16'. As shown in FIG. 4, the motorised ball valve (18') and its corresponding motor are housed in a separate housing 36.

The body of the piston 16 may include a calibration element which is disposed within the sample chamber, within "sight" of the optical testing apparatus, when the piston is in its extended position.

Typically, the devices are adapted to follow a testing procedure as set out below. The devices will generally be controlled by electronics on a control PCB which may be housed in housing 34, although in some embodiments might be externally mounted, for example if the device is to be integrated into a boiler. The control PCB may include a microcontroller, or any other suitable type of control circuitry.

The process begins with the piston 16 in its fully-extended position, with the sample chamber empty.

First, the excitation light source 20 is switched on. This excites a fluorescent coating on the calibration element which forms part of the body of the piston 16. The fluorescent coating emits light at (for example) a wavelength of 405 nm. The intensity of the 405 nm radiation is measured by the detector 22. Because the intensity of the excitation light source 20 and the fluorescent properties of the coating on the calibration element are known with some accuracy, the measurement from the detector 22 can be used to calibrate the device 10, effectively accounting for any dirt which may have built up on the borosilicate glass walls 14a. Once the calibration reading is taken, the excitation light source 20 can be turned off.

The piston 16 is then retracted, drawing a sample of water into the sample chamber 14. In the first embodiment (FIG. 1), this also has the effect of moving the integrated valve 18 to meet the valve seat 18a, to seal off the sample chamber 14 from the central heating system circuit. In the alternative embodiment (FIG. 3), the motorised ball valve 18' will have to be operated at this stage to seal off the sample chamber from the central heating system circuit.

Once the water sample is in the sample chamber 14, it is left to cool and settle for a period of time. This time period may be 5 minutes, or 10 minutes, or another period. The purpose of the delay is to allow any solids to settle out of the sample, so that turbidity does not affect the results of the test. It may also be necessary to allow the sample to cool, depending on the optical property being tested and the chemical being used.

The excitation light source is then switched on to excite the sample. This results in fluorescence of the sample, depending on the concentration of the selected chemical present. It will be appreciated that fluorescence is not the only optical property which can be used to test the concentration of a selected chemical. Absorption and phosphorescence are other potentially-suitable properties.

The detector then measures the intensity of emitted light at (for example) 405 nm, which is the expected fluorescent emission wavelength of the tracer chemical in one particular embodiment. Preferably, several measurements are taken, for example three measurements over 10 to 20 seconds. Taking an average of multiple measurements can help to ensure consistent results. Once all measurements are taken, the excitation light source is turned off.

After testing is complete, the motorised ball valve 18' (where applicable) is opened, and the piston 16 is extended to empty the sample chamber 14. The wiper seal 16a cleans the inside of the borosilicate glass walls 14a as the piston 16 extends.

The readings from the detector 22 are assessed. In a simple embodiment, it is simply determined whether or not the level of the chemical is acceptable or not. A simple output interface might comprise a green LED for acceptable and a red LED for inadequate. Alternatively, the results might be transferred to a follow-on system, for example a boiler data management system, via a wired or wireless connection. In some embodiments, an electronic signal may be sent to a dosing device to cause dosing of the system with inhibitor, when an insufficient concentration is detected.

Figure 5:
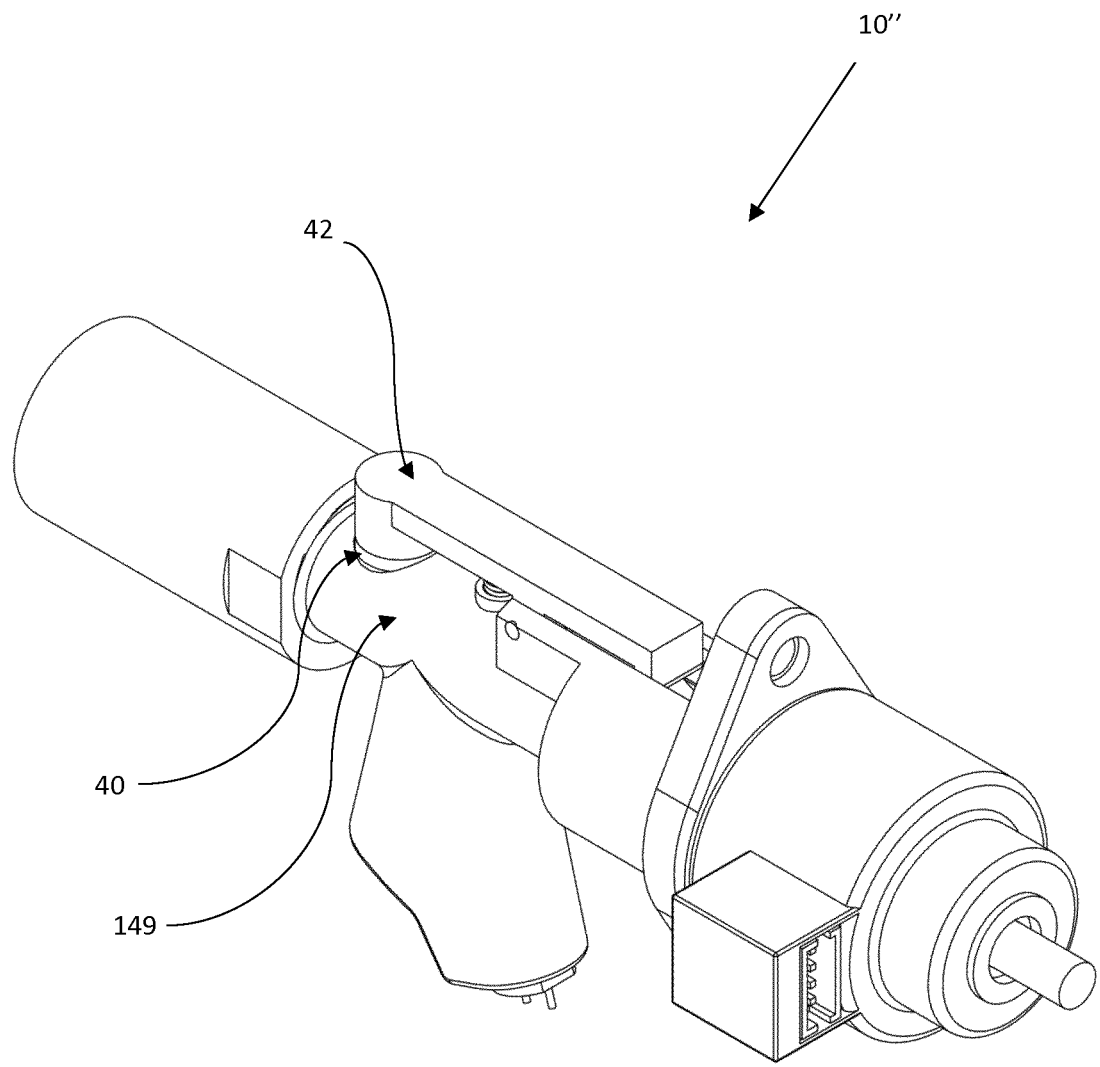
FIG. 5 shows a perspective view of a third embodiment of a testing device according to the first aspect of the invention.
Figure 6:
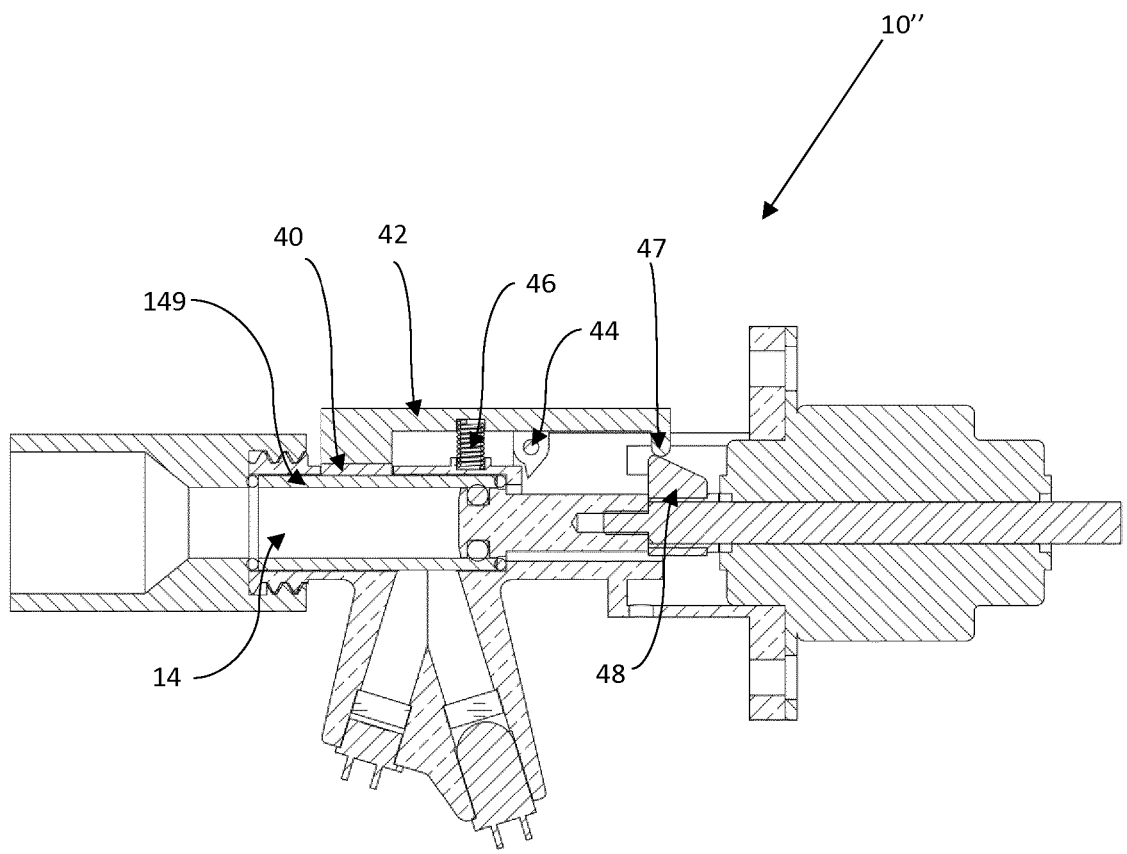
FIG. 6 shows a cross section through the device of FIG. 5.

Referring now to FIG. 5 and FIG. 6, yet another embodiment of a testing device is indicated at 10". This embodiment is substantially identical to testing device 10' of FIG. 3 and FIG. 4, but includes a movable magnet 40. The magnet 40 is provided at one end of a pivoting arm 42, and by pivoting the arm the magnet may be moved from an in-use position, in which the magnet 40 is in contact with the wall 14*a* of the sample chamber 14, to an out-of-use position where the magnet is spaced away from the wall 14*a* of the sample chamber 14. It is the in-use position which is illustrated in FIG. 5 and FIG. 6.

The magnet in the in-use position contacts the outside of the wall 14*a* of the sample chamber through a hole in the opaque overmoulding. A light-tight seal is preferably provided to prevent leakage of light into the sample chamber. Alternatively, a light-tight external casing may be relied on to prevent ambient light leaking into the sample chamber.

As seen most clearly in FIG. 6, the pivoting arm is connected to the body of the testing device at a pivot 44. Between the pivot 44 and the magnet 40, a spring 46 is provided which urges the magnet end of the pivoting arm away from the wall of the sample chamber, i.e. into the out-of use position. At the other (non-magnet) end of the pivoting arm, a follower 47 is provided. The follower 47 contacts a linear cam 48, which in turn moves linearly with the piston 16. The linear cam 48 is positioned to lift the follower away from the body of the testing device when the piston 16 is retracted to fill the sample chamber 14. By lifting the follower away from the body of the testing device, the magnet 40 on the other end of the pivoting arm is moved into contact with the wall 14*a* of the sample chamber 14, against the action of the spring 46. In this way, the magnet 40 is positioned in contact with the wall 14*a* of the sample chamber 14, whenever the syringe is retracted and the sample chamber is full of liquid.

The magnet attracts any magnetic particles which may be entrained in the water sample being tested, and prevents the entrained magnetic particles from adversely affecting the testing procedure.

Figure 7:
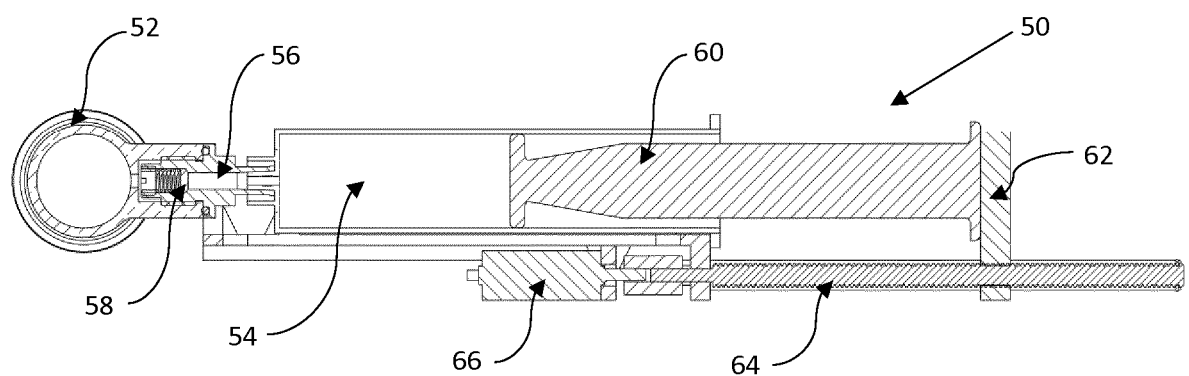
FIG. 7 shows a cross section through a first embodiment of a dosing device according to the third aspect of the invention.

Referring now to FIG. 7, a dosing device according to the third aspect of the invention is indicated generally at 50. The dosing device includes a fitment 52 for connecting the dosing device 50 into a central heating system circuit, a chemical reservoir 54 in the form of a syringe, and a passageway 56 between the syringe 54 and the fitment 52. A one-way check valve 58 is provided in the passageway 56. The check valve 58 allows fluid to flow out of the syringe 54 into the central heating system circuit, but prevents flow out of the central heating system circuit into the syringe 54.

The syringe 54 includes a piston 60, which can be extended into the syringe 54 (i.e. moved leftwards in FIG. 7) in order to force liquid from the syringe 54, through the passageway 56 and valve 58, into the central heating system circuit via the fitment 52.

The syringe piston 60 may be pushed into the syringe body by an arm 62. The arm 62 includes a screw threaded aperture. An externally screw threaded rod 64 passes through the aperture, and is fixed at one end to the shaft of an electric motor 66 which in turn is fixed relative to the syringe body 54. In this way, the electric motor can rotate the threaded rod 64 in order to move the arm 62 linearly, to extend the piston 60 into the syringe 54 and force inhibitor chemical from the syringe 54 into the central heating system circuit.

The syringe 54 is removable from the passageway 56 so that the syringe may be refilled with inhibitor chemical when empty. With the syringe removed, the check valve 58 will always be closed, preventing any leakage of water out of the central heating system circuit.

Figure 8:
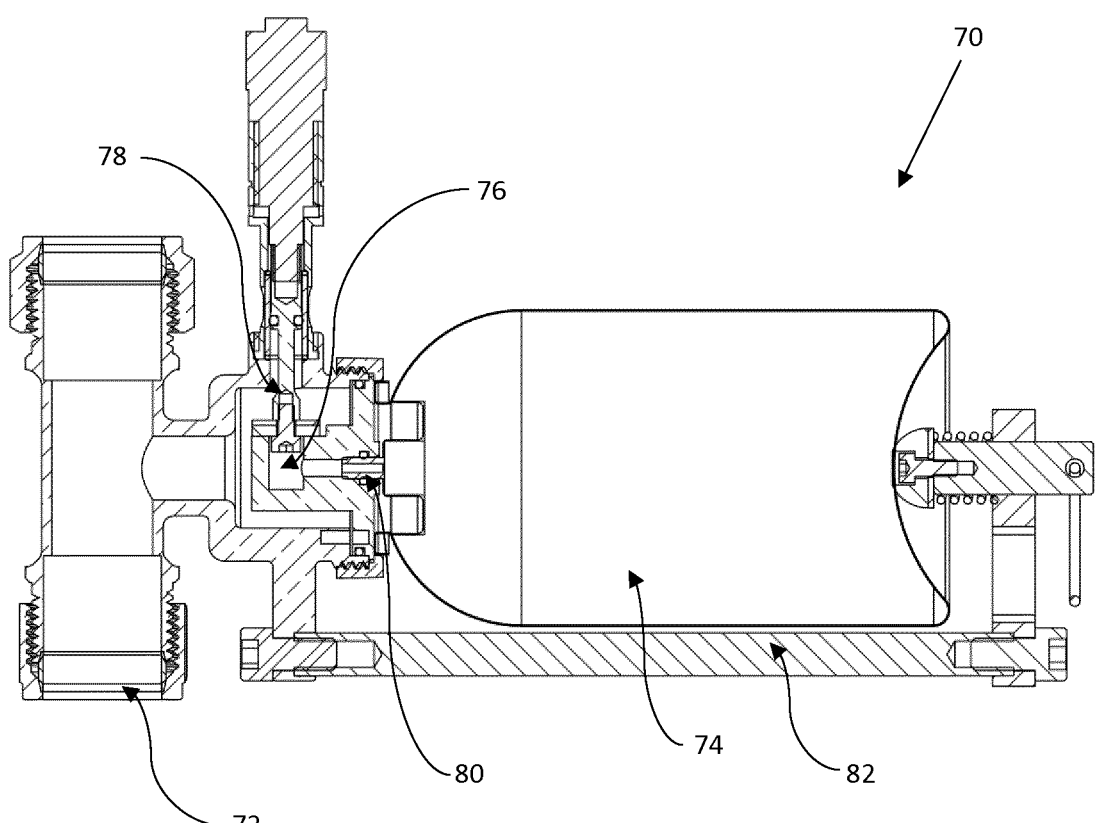
FIG. 8 shows a cross section through a second embodiment of a dosing device according to the third aspect of the invention.

Referring now to FIG. 8, a second embodiment of a dosing device is indicated generally at 70. The dosing device 70 again includes a fitment 72 for connection to a central heating system, a reservoir 74 containing inhibitor chemical, a passageway 76 between the reservoir 74 and the central heating system circuit, and a valve 78 in the passageway 76. However, in this embodiment the reservoir is a pressurised canister and the valve is a motorised valve. In response to the electronic signal, the valve 78 opens and, because of the greater static pressure on the reservoir side, fluid will flow from the reservoir into the central heating system. The valve 78 can be opened for a period of time to control the amount of inhibitor chemical which is dosed into the central heating system.

The pressurised canister 74 includes a nozzle 80 with a push-to-open valve. A seat is provided on the entrance to the passageway 76, and when the canister is fitted the nozzle 80 is pushed onto the seat to hold the push-to-open valve permanently open while the canister 74 is attached to the dosing device 70. The canister 74 is held onto the rest of the device 70 and against the seat on the entrance to the passageway 76 by means of a clamp 82 which extends from the fitment 72, along the outside of the canister and behind the canister, to push the canister against the seat. The clamp 82 may be spring-loaded to allow quick release of the canister. When the canister is removed, the valve on the nozzle 80 will close to prevent any leakage. It is envisaged that disposable canisters will be supplied full of inhibitor chemical, and when the canister is empty it will be discarded and replaced with a new, full, pressurised canister.

Figure 9:
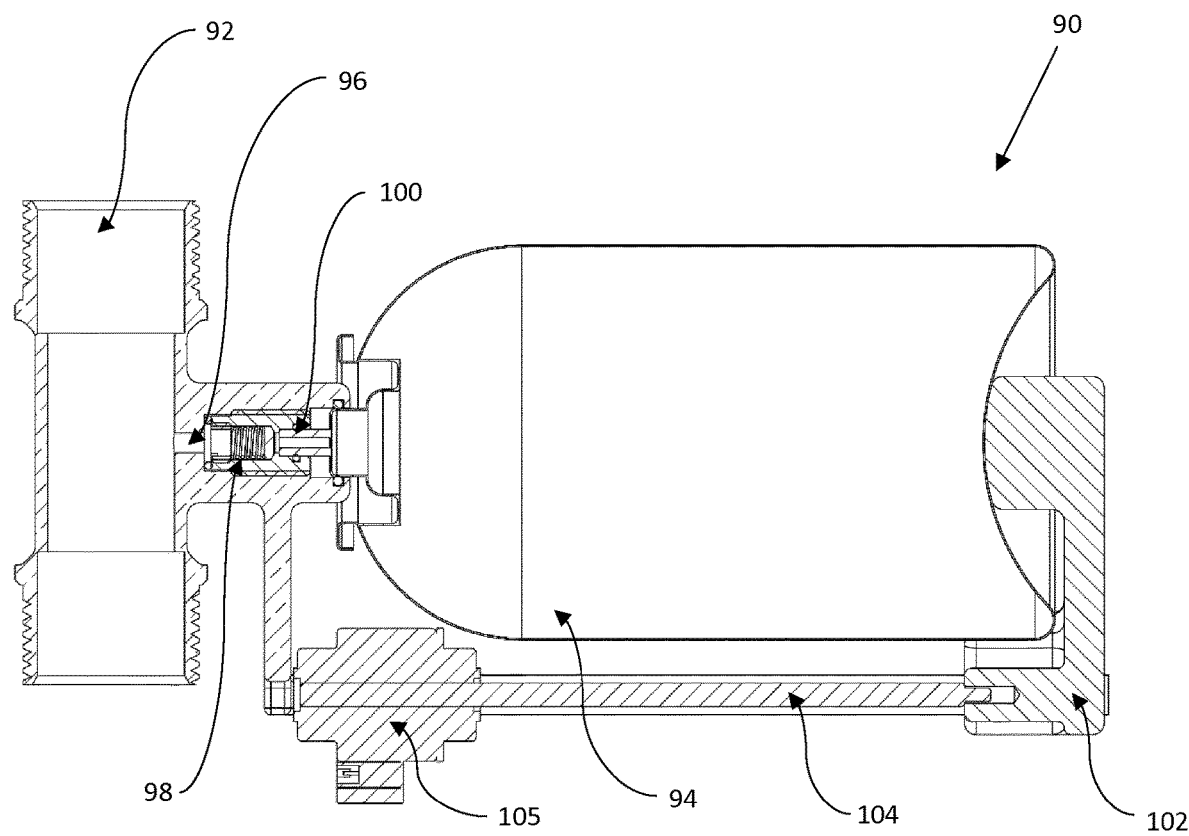
FIG. 9 shows a cross section through a third embodiment of a dosing device according to the third aspect of the invention.

Referring now to FIG. 9, a third embodiment of a chemical dosing device is indicated generally at 90. The dosing device includes a fitment 92 for connection to a central heating system circuit, a reservoir 94 which in this embodiment is a pressurised canister with a push-to-open valve on the nozzle, similar to the canister (74) of the second embodiment, a passageway 96 in the fitment between the canister 94 and the central heating system circuit, and a check valve 98 in the passageway 96. The canister 94 is disposed with the nozzle 100 seated on the entrance to the passageway 96, such that when the canister 94 is pushed towards the entrance to the passageway 96, the valve on the nozzle 100 will open and chemical will be admitted into the passageway 96, through the check valve 98, and into the central heating system circuit 92.

The canister 94 is held against the entrance to the passageway 96 by means of a clamping and actuation arrangement 102. At one end the clamping and actuation arrangement is fixed to the fitment. A retractable member 104 extends from the fitment 92, alongside the outside of the canister 94 (underneath the canister 94 in FIG. 9) and then behind the canister, where it holds the canister 94 from behind. By retracting the retractable member 104, the nozzle 100 of the canister is pushed against the seat on the entrance to the passageway 96, to open the push-to-open valve. The retractable member 104 is retracted by an actuator 105. The actuator may be a motor with a screw threaded rod, or alternatively the actuator may be a solenoid or other linear actuator. The actuator operates in response to an electronic signal to retract the rod, push the canister 94 against the entrance to the passageway 96, and dose the heating system with inhibitor chemical from the canister 94.

The testing device and dosing device may work together to protect a heating system. When the testing device detects that the central heating system is insufficiently dosed with inhibitor chemical, it may send an electronic signal to the dosing device to cause dosing of the system with inhibitor, to correct the dosing level before significant corrosion is allowed to occur. The testing device and dosing device in some embodiments may be combined into a single housing, and/or may share a single fitment for connection to the central heating system circuit.

The embodiments described above and illustrated in the figures are only examples of how the invention might be put into practice. Various modifications will be apparent to the skilled person. The invention is defined in the claims.

The invention claimed is:

1. A testing device for testing a level of a selected chemical in a central heating system water in a central heating system circuit, the testing device comprising:
a sample chamber for holding a sample of central heating system water to be tested, the sample chamber being connected to the central heating system circuit to allow fluid to pass between the central heating system circuit and the sample chamber;
a piston for controlling filling of the sample chamber with the central heating system water from the central heating system circuit, and emptying of the sample chamber, the piston being movable to a retracted position for drawing water out of the central heating system circuit into the sample chamber, and to an extended position for emptying the sample chamber and returning the water to the central heating system circuit;
at least one valve for isolating the sample of central heating system water from the central heating system circuit during testing; and
an optical testing apparatus including a light source and a detector, for measuring an optical property of the sample of central heating system water isolated within the sample chamber and thereby making a determination as to whether or not the level of the selected chemical in the water is greater than a predetermined threshold level,
wherein the valve for isolating the sample during testing is integrated into the piston, and
wherein a sealing element on the piston seals the entrance to the sample chamber where the piston is in a retracted position, for preventing any further flow between the sample chamber and the central heating system circuit.

2. The testing device of claim 1, wherein the selected chemical is a corrosion inhibitor.

3. The testing device of claim 1, wherein the sample chamber is emptied by returning the central heating system water in the sample chamber to the central heating system circuit.

4. The testing device of claim 1, wherein a single flow passage is provided between the sample chamber and the central heating system circuit, to allow fluid to pass in both directions between the central heating system circuit and the sample chamber.

5. The testing device of claim 1, wherein the piston includes a wiper seal for sealing against and cleaning the internal walls of the sample chamber.

6. The testing device of claim 1, wherein the piston includes a necked-down section in front of the piston crown, and the sealing element being attached to the piston crown via the necked-down section.

7. The testing device of claim 6, wherein the necked-down section is located asymmetrically to a one side of the piston, in front of the piston crown.

8. The testing device of claim 1, wherein a control means is provided and adapted to control the testing device for fully-automated testing, including drawing water from the central heating system circuit into the sample chamber, sealing the sample chamber, testing the sample with the optical testing apparatus, and opening the valve and emptying the chamber.

9. The testing device of claim 8, wherein the control means is adapted to wait for a period of time between closing the valve and testing the sample with the optical testing apparatus.

10. The testing device of claim 9, wherein the period of time is at least one minute.

11. The testing device of claim 1, wherein the level of the selected chemical is determined indirectly, by using the optical testing apparatus to measure a concentration of a tracer chemical which has been added to the selected chemical in a known concentration.

12. The testing device of claim 11, wherein the tracer chemical is 1,3,6,8 Pyrenetetrasulfonic acid tetrasodium salt (PTSA).

13. The testing device of claim 1, wherein the light source and detector are disposed at an acute angle to each other, facing into the sample chamber.

14. The testing device of claim 1, wherein at least one filter is provided on at least one of the detector and the light source.

15. The testing device of claim 1, wherein the optical property is fluorescence.

16. The testing device of claim 1, wherein a calibration element is provided within the sample chamber.

17. The testing device of claim 16, wherein the calibration element is moved automatically into the sample chamber where the sample chamber is emptied, and moved out of the sample chamber where water is drawn into the sample chamber for testing.

18. The testing device of claim 17, wherein the calibration element is provided as part of the piston.

19. The testing device of claim 1, wherein a magnet is provided for attracting any magnetic particles entrained in water in the sample chamber.

20. The testing device of claim 19, wherein the magnet is movable between an in-use position adjacent to the sample chamber and an out-of-use position spaced from the sample chamber.

21. The testing device of claim 20, wherein the magnet is movable on a pivoting arm.

22. The testing device of claim 21, wherein the pivoting arm is arranged to automatically pivot as the piston is operated to draw fluid into and out of the sample chamber, so that the magnet is in the in-use position where the chamber is full and in the out-of-use position where the chamber is empty.

23. The testing device of claim 1, further comprising a reservoir of the selected chemical, and a means for introducing a quantity of the selected chemical into the central heating system circuit, in response to a determination by the optical testing apparatus that the concentration of the selected chemical in tested water is inadequate.

\* \* \* \* \*